United States Patent [19]

DeGraff

[11] 4,384,157

[45] May 17, 1983

[54] CATALYTIC CONDENSATION PROCESS WITH PROPANE PRODUCT STREAM

[75] Inventor: Richard R. DeGraff, Deerfield, Ill.

[73] Assignee: UOP Inc., Des Plaines, Ill.

[21] Appl. No.: 364,108

[22] Filed: Mar. 31, 1982

[51] Int. Cl.³ .......... C07C 3/16

[52] U.S. Cl. .......... 585/514; 585/510; 585/529

[58] Field of Search .......... 585/514, 510, 529

[56] References Cited

U.S. PATENT DOCUMENTS

| | | | |
|---|---|---|---|
| 3,137,739 | 6/1964 | Paulis et al. | 585/529 |
| 3,296,121 | 1/1967 | Potts | 208/350 |
| 3,437,708 | 4/1969 | Gantt | 585/450 |
| 3,673,111 | 6/1972 | Hovarth et al. | 585/529 |
| 4,137,274 | 1/1979 | Mikulicz et al. | 585/529 |

OTHER PUBLICATIONS

Petroleum Processing Principles and Applications, R. J. Hengstebeck, McGraw-Hill Book Company, Inc., 1959, pp. 208-218.

*Primary Examiner*—Curtis R. Davis

*Attorney, Agent, or Firm*—James R. Hoatson, Jr.; John F. Spears, Jr.; William H. Page, II

[57] ABSTRACT

A process is disclosed for the catalytic condensation of propylene to produce $C_6$-plus hydrocarbons. The process consumes all of the propylene present in a mixed propane-propylene feed stream and produces a high purity propane effluent stream. The effluent of the reaction zone is flashed with the resultant vapor being recycled to the reaction zone and the remaining liquid being passed into a fractionation column. A $C_3$ sidecut is removed from the column and stripped to remove propylene, which is returned to the column. The overhead stream of the column is also recycled to the reaction zone.

10 Claims, 1 Drawing Figure

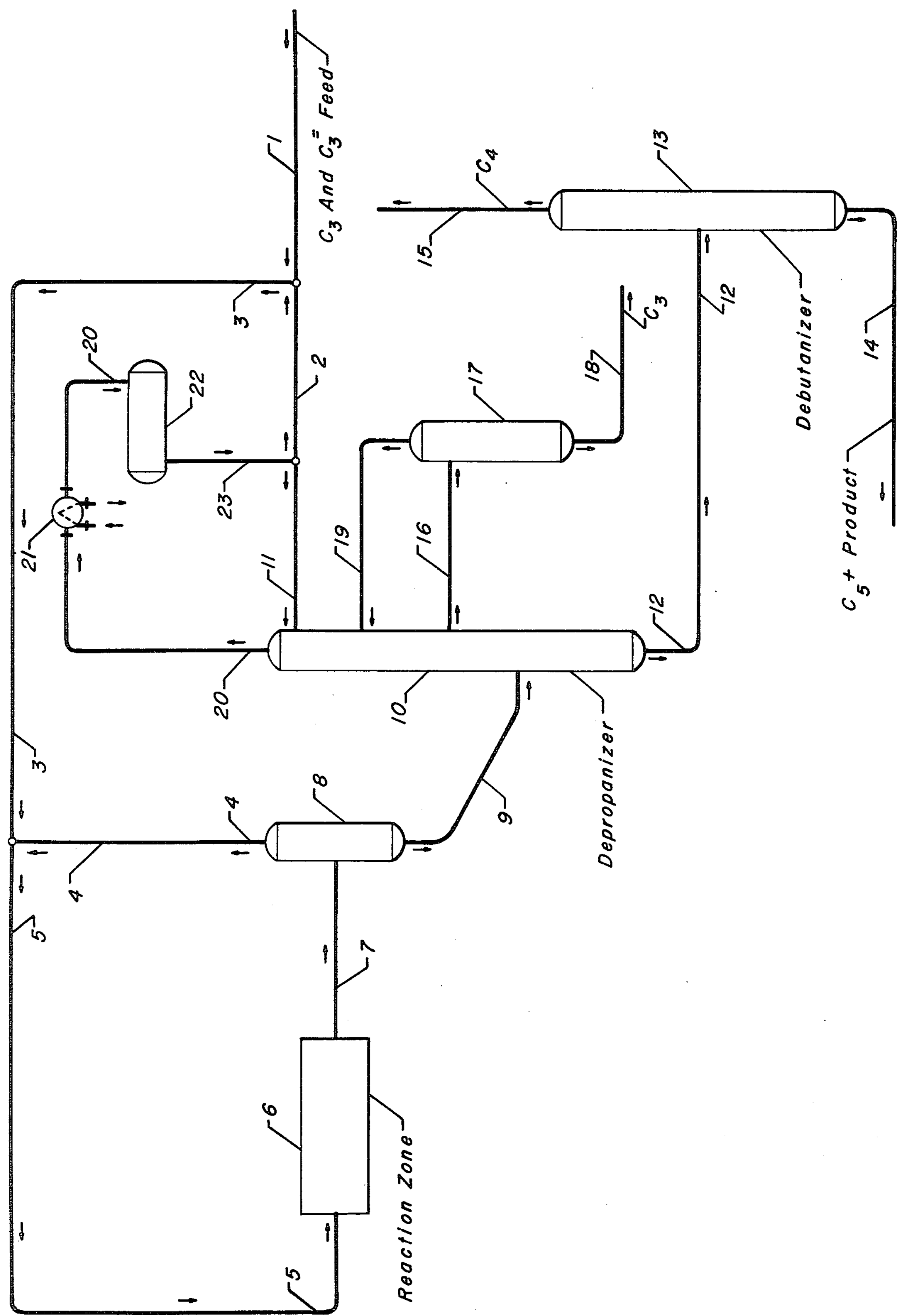
$C_3$ And $C_3^=$ Feed
Reaction Zone
Depropanizer
Debutanizer
$C_4$
$C_3$
$C_5^+$ Product

CATALYTIC CONDENSATION PROCESS WITH PROPANE PRODUCT STREAM

FIELD OF THE INVENTION

The invention relates to a hydrocarbon conversion process commonly referred to as catalytic condensation in which light olefinic hydrocarbons are reacted to produce heavier hydrocarbons. The invention more directly relates to the catalytic condensation of propylene contained in a mixed propane-propylene feed stream to product $C_6$-plus acyclic hydrocarbons which are suitable for use as motor fuels including gasoline. The invention is specifically concerned with maximizing the consumption of propylene in such a process and in simultaneously producing a high purity propane product stream which meets certain commercial quality specifications.

PRIOR ART

The catalytic condensation of light olefins is an established commercial process used to produce gasoline blending components. It is described at pages 208 to 218 of "Petroleum Processing, Principles and Applications" by R. J. Hengstebeck, McGraw-Hill Book Co., Inc. 1959. This description includes a drawing at page 212 which shows the effluent of the reaction zone being passed into a depropanizer column, with a first portion of the depropanizer net overhead stream being recycled to the reaction zone and a second portion being withdrawn from the process. The net bottoms stream of the depropanizer is passed into a debutanizer column. This reference also indicates propylene is a satisfactory feedstock and that mixtures of paraffins and olefins are the normal reaction zone charge stock.

U.S. Pat. No. 3,437,708 illustrates a separation process for the product of an aromatic hydrocarbon alkylation zone or of an oligomerization zone. This reference is pertinent for its showing that the effluent stream of the reaction zone may be flashed to a considerably lower pressure before entering a vapor-liquid separation zone located between the reaction zone and the depropanizer column. The propane flashed off the depressurized liquid together with previously uncondensed propane is indirectly collected in a receiver and recycled as a liquid. This recycling of propane from an intermediate flash zone is also practiced commercially in catalytic condensation motor fuel plants.

The use of a separate fractionation column or stripping column to remove a more volatile compound from a sidecut stream removed from a fractionation column is a known commercial practice. It is often used on a crude oil fractionation column. U.S. Pat. No. 3,296,121 illustrates this use of a sidecut stripping column to remove volatile compounds from separate gas oil and naphtha streams.

BRIEF SUMMARY OF THE INVENTION

The invention provides an improved process for the catalytic condensation of propylene contained in propylene-propane mixtures or in feed streams containing both propylene and butylene. The subject process has the advantage of consuming essentially all of the propylene which is charged to the process. It also has the advantage of producing a high purity propane stream which is suitable for retail sale as bottled LPG used in small heating devices.

One embodiment of the invention may be broadly characterized as comprising the steps of passing a high purity $C_3$ feed stream comprising propylene and propane, a recycle stream which also comprises propane and propylene and a hereinafter characterized first net fractionation column overhead stream into a catalytic condensation reaction zone wherein the entering hydrocarbons are contacted with a catalyst at conditions effective to produce a reaction zone effluent stream comprising propane, propylene and $C_6$-plus hydrocarbons; separating the reaction zone effluent stream into a vapor-phase stream, which is returned to the catalytic condensation reaction zone as the recycle stream, and a liquid-phase stream comprising propane, propylene and $C_6$-plus hydrocarbons; passing the liquid-phase stream into a first fractionation column; passing a sidecut stream comprising propane and propylene and which is withdrawn above the feed point of the first column into a stripping column wherein the sidecut stream is separated into a second net overhead stream which is passed into the first fractionation column and a first net bottoms stream which is substantially free of propylene, and withdrawing the first net bottoms stream from the process; withdrawing from the first fractionation column a second net bottoms stream which is substantially free of propane and which comprises the product $C_6$-plus hydrocarbons; and, forming a net overhead liquid stream which comprises propylene and propane from an overhead vapor stream removed from the first fractionation column, and passing the net overhead liquid stream into the catalytic condensation zone as the first net fractionation column overhead stream.

BRIEF DESCRIPTION OF THE DRAWING

The Drawing illustrates the preferred embodiment of the invention. However, it is not intended to limit the scope of the inventive concept to the particular flow shown or to exclude those other embodiments described herein or which result from the normally expected modification of this one particular flow.

Referring now to the Drawing, a $C_3$ feed stream comprising a mixture of propane and propylene, and normally containing more propane than propylene, is passed into the process through line 1. This stream is admixed with the net fractionation column overhead stream flowing through line 2 and the admixture is transferred through line 3. The admixture is then combined with a recycle stream comprising propane and propylene from line 4, which is preferably a liquid stream as described herein. The admixture of these three streams is then preferably heat exchanged against the contents of line 7 in an indirect heat exchange means not shown and then passed into the catalytic condensation reaction zone 6 through line 5.

Propylene is contacted with a catalyst within the catalytic condensation zone under suitable catalytic condensation conditions to effect the production of a catalytic condensation reaction zone effluent stream carried by line 7. This stream comprises unreacted propylene, essentially inert propane and various reaction products including the desired $C_6$ hydrocarbons, $C_9$ hydrocarbons and other compounds. The catalytic condensation zone effluent stream is preferably cooled and then flashed to a lower pressure to form a mixed-phase stream passed into the vapor-liquid separator 8. The vaporous components of the catalytic condensation zone effluent stream are recycled, preferably by means not shown, through line 4 and the liquid components are passed into a fractionation column 10 referred to as a depropanizer through line 9. The liquid stream of line 9 will contain dissolved propane and propylene and substantially all of the $C_6$-plus product hydrocarbons.

A sidecut stream is withdrawn from the fractionation column through line 16 at an upper intermediate point of the column and passed into a sidecut stripping column 17. This column is designed and operated to concentrate essentially all the propylene which enters the sidecut column into an overhead vapor stream returned to column 10 through line 19. The remainder of the sidecut stream is essentially propane and is removed from the sidecut column as a bottoms stream withdrawn from the process as a high purity LPG product stream via line 18. The net bottoms stream of the fractionation column 10 comprises essentially all of the $C_4$-plus hydrocarbons which enter the fractionation column including any butane which is present in the feed stream. This material is transferred into the debutanizer column 13 through line 12 and therein separated into a net overhead stream of line 15 comprising butane and a $C_5$-plus product stream removed in line 14. This stream contains the $C_6$-plus hydrocarbons produced in the catalytic condensation zone.

An overhead vapor stream comprising propylene and propane is removed from the depropanizer 10 through line 20 and passed through the overhead condenser 21. This results in the condensation of essentially all of the overhead vapor stream and the formation of an overhead liquid which is collected in the overhead receiver 22. The overhead liquid is withdrawn through line 23 and divided into a first portion returned to the column as reflux through line 11 and a second portion carried by line 2 which is the net overhead liquid stream of column 10. This second portion is recycled to the reaction zone 6 to allow the consumption of its propylene content. Any relatively noncondensible gas such as ethane which enters the process may be removed as a small vent stream not shown withdrawn from the overhead receiver.

DETAILED DESCRIPTION

Catalytic condensation processes are useful in converting propylene, butylene or propylene-butylene mixtures into higher molecular weight hydrocarbons of greater economic value. They are used to convert propylene into "trimer" or "tetramer" which may be used to manufacture detergents. Catalytic condensation processes can also be utilized to produce good quality gasoline blending components from propylene, and it is this specific form of the catalytic condensation process which is the subject of the inventive concept.

The feed stream to a catalytic condensation process is typically a mixture of the feed olefin and a paraffin or paraffins of the same carbon number. The catalytic condensation reaction for gasoline production does not consume all of the olefin present in the feed stream, and the effluent stream of the catalytic condensation reaction zone will therefore comprise a mixture of the unreacted olefin and relatively unreactive paraffins. Heretofore, for a $C_3$ catalytic condensation process the effluent of the reaction zone has been basically separated into one or more $C_3$ recycle streams comprising propane and propylene, an off gas or light effluent stream which also comprises both propane and propylene and a $C_5$-plus product stream. The presence of propylene in the $C_3$ or light effluent stream of the process indicates that all of the more valuable propylene is not being consumed in the reaction zone. A second disadvantage of this present mode of operation is that the propylene-containing $C_3$ effluent stream does not meet the quality specifications which have been established for the retail sale of LPG used in small heating devices.

It is therefore an objective of the subject invention to provide an improved catalytic condensation process for the production of motor fuel blending components from propane-propylene mixtures. It is a further objective of the subject invention to provide a catalytic condensation process in which essentially all propylene charged to the process is converted into $C_6$-plus hydrocarbons. It is another objective of the subject invention to provide a catalytic condensation process which produces a substantial olefin-free LPG product stream.

The feed stream to the subject invention comprises a mixture of propane and propylene or a mixture comprising both propylene and butylenes. Preferably, this is a rather pure stream which contains very little (less than 5 percent) of any hydrocarbons having other than 3 carbon atoms per molecule. Any hydrocarbons other than propane and propylene preferably have more than 3 carbon atoms per molecule. It is especially preferred that the feed stream contains between about 10 and 65 mole percent propylene. However, the benefits of the inventive concept are also achieved when the feed stream contains butylenes. The feed stream may therefore comprise a mixture of propylene and up to about 50 mole percent butylene plus associated paraffins. The following description of the inventive concept is cast mainly in terms of the preferred propylene feed but also applies to mixed propylene-butylene feeds.

The propylene-containing feed stream is combined with two other process streams either before entering or upon entering the reaction zone of the process. These two streams are the net overhead liquid removed from the depropanizer column used in the process and a recycle stream separated from the effluent of the reaction zone upstream of the depropanizer. Both of these streams will be a mixture of propane and propylene. These three streams are then passed into a reaction zone wherein they are contacted with a catalyst which is effective in causing propylene molecules to react with other propylene molecules to form $C_6$ and $C_9$ hydrocarbons while the propane is essentially unchanged. The propylene is thereby selectively consumed in the subject process.

The catalytic condensation reaction zone may take many forms depending on such variables as the catalyst which is employed within this zone. For instance, U.S. Pat. Nos. 3,932,553 and 3,997,621 describe processes in which boron trifluoride is utilized as a catalyst. Both of these catalytic systems utilize a minor amount of an additive to control the extent to which the reaction proceeds. In both of these references, the catalyst system appears to be homogeneous. Heterogeneous catalytic systems for the production of higher molecular weight olefins by the oligomerization or dimerization of light olefins are described in U.S. Pat. Nos. 3,906,053; 3,916,019; 3,959,400; 3,981,940 and 3,981,941. As may be expected from the large number of processes, the conditions employed within the reaction zone may vary widely. For instance, the just cited references specify that the reaction may be performed at temperatures ranging from $-50°$ to $250°$ C. and at a pressure ranging from about 1.3 to approximately 100 atmospheres gauge.

The preferred catalyst for use in the subject process is an SPA (solid phosphoric acid) type catalyst. As used herein, the term "SPA catalyst" is intended to indicate a solid catalyst which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are however possible. Further details as to the composition and production of SPA catalysts may be obtained from U.S. Pat. Nos. 3,050,472; 3,050,473 and 3,132,109 and from other references.

The catalyst is preferably disposed in fixed beds. Either a tubular or chamber-type reactor structure may be used. In a tubular reactor, the catalyst is placed in relatively small diameter tubes which are surrounded by a water jacket to remove the heat liberated by the exothermic reaction. Steam generated in this manner can be used to preheat the feed. In a chamber-type reactor, the reactants flow through a series of large diameter catalyst beds. The temperature of the reactants is controlled by recycling relatively inert hydrocarbons (propane) which act as a heat sink and/or by the use of a quench between vertically stacked catalyst beds. The quench material is the same as that used as the recycle stream, and both methods of temperature control may be used simultaneously. The different catalyst beds are preferably contained within a single, cylindrical, vertically oriented vessel, and the feed stream preferably enters the top of the reactor. A chamber-type reactor containing about five catalyst beds is preferred. Separate parallel reactors may be used in large process units.

The reaction zone may be maintained at widely varying conditions due to the previously listed variables including the use of different catalysts. A broad range of suitable pressures is from about 15 to about 1200 psig, with a preferred pressure range for an SPA catalyst being from 400 to 1000 psig. The temperature maintained in this zone with the preferred SPA catalyst may vary from about 120° to about 260°. Steam or water may be fed into the reactor to maintain the desired water content in the preferred catalyst.

In the preferred embodiment, an SPA catalyst is utilized to form an effluent containing primarily $C_6$ and $C_9$ olefinic hydrocarbons having boiling points within a gasoline boiling point range of about 43° to about 215° C. as determined by the appropriate ASTM distillation method. Preferably, the feed stream is first heat exchanged with the reactor effluent, further heated and then passed into the top of the reactor. Additional amounts of a propane coolant similar in composition to the recycle stream are preferably added between each of the catalyst beds.

The effluent of the reaction zone is preferably first cooled by indirect heat exchange against the feed stream to the reaction zone and then flashed to a substantially lower pressure than the reaction zone. The pressure reduction during the flashing of the effluent stream is preferably between about 150 and about 300 psi. This sequence of steps should produce a mixed-phase stream in which the very great percentage of the $C_6$-plus hydrocarbons are present in a liquid-phase which also contains substantial amounts of propane and propylene. This mixed-phase stream is then separated into a vapor-phase stream which is made up mainly of propane and propylene and a liquid-phase stream made up of all the liquid remaining after the flashing step. If the feed stream contains significant amounts of butylene then the vapor stream will also contain butylene. The contents of the vapor-phase stream are returned to the reaction zone as a recycle stream. The vapor-phase stream may be recycled directly by simple compression and admixture into the feed stream. However, it is preferred that the vapor-phase stream is first condensed and then pressurized by a pump prior to admixture into the feed stream since this more complicated procedure is normally justified by lower utilities cost of recycling this $C_3$ stream. That is, the lower utilities cost of this method compares favorably to its higher capital cost. The separation of the vapor and liquid present after flashing the reaction zone effluent stream is preferably performed in a vapor-liquid separation zone comprising a single vertical vessel of adequate size and construction to accomplish this separation.

The liquid-phase stream separated from the reaction zone effluent stream is passed into an intermediate point of a first fractionation column referred to herein as a depropanizer. This intermediate point is separated from both the upper and the lower ends of the depropanizer by at least three fractionation trays. One function of the depropanizer is to concentrate all of the $C_4$-plus hydrocarbons which enter the column into a net bottoms stream which is substantially free of $C_3$ hydrocarbons. The net bottoms stream of the first fractionation column will therefore contain substantially all of any butanes, pentanes, hexanes, hexenes, nonanes or nonenes which enter the column. The net bottoms stream of the depropanizer is normally passed into a debutanizer column which is also referred to herein as the second fractionation column. The debutanizer column separates the entering hydrocarbons into a net overhead stream which is rich in $C_4$ hydrocarbons and another net bottoms stream containing substantially all of the $C_6$-plus hydrocarbons produced in the reaction zone but substantially free of $C_4$ hydrocarbons. In a commercial unit this bottoms stream comprises a wide variety of hydrocarbons containing up to 15 carbon atoms per molecule. These hydrocarbons are primarily olefinic and are normally used as a gasoline blending component. However, if desired they could be passed into a catalytic hydrogenation zone to effect their saturation.

A liquid-phase sidecut is removed from an intermediate point above the feed point of the depropanizer and passed into the top of a stripping column. This stripping column functions to separate the entering hydrocarbons, which are mainly propane and propylene, into a net bottoms stream which is substantially free of propylene and an overhead stream which is preferably passed directly into the depropanizer as a vapor-phase stream. The bottoms stream of the stripping column should contain less than about 5 mole percent propylene. This bottoms stream may then be sold as high quality bottled propane LPG suitable for use in small heating devices. When properly designed and operated a reboiled column having about 40 real trays will function well as the stripping column.

Essentially all of the propylene entering the depropanizer column is concentrated into the overhead vapor stream. Representative conditions for this overhead vapor stream as it is removed from the column include a pressure of about 250 psig and a temperature of about 120° F. (49° C.). This overhead vapor passes into the customary overhead condenser and is cooled and condensed to form a liquid rich in $C_3$ hydrocarbons collected in the overhead receiver. This liquid is divided into a reflux stream and second stream referred to herein as the net fractionation column overhead stream, which is passed into the reaction zone.

The preferred embodiment of the invention may be characterized as a hydrocarbon conversion process which comprises the steps of passing a feed stream comprising propylene and propane, a hereinafter characterized recycle stream, and a hereinafter characterized net fractionation column overhead stream into a catalytic condensation reaction zone wherein propylene is contacted with a catalyst at conditions effective to produce a reaction zone effluent stream comprising propylene, propane and $C_6$-plus hydrocarbons; cooling and then flashing the reaction zone effluent stream to a pressure at least 100 psi below the pressure maintained in the reaction zone; separating the reaction zone effluent stream in a vapor-liquid separation zone into a vapor-phase stream comprising primarily propylene and propane and a liquid-phase stream comprising $C_6$-plus hydrocarbons, propane and propylene; passing the contents of the vapor-phase stream into the reaction zone as the previously referred to recycle stream; passing the liquid-phase stream into a first intermediate point of a first fractionation column; withdrawing a sidecut stream comprising propane and propylene from the first fractionation column at a higher second intermediate point and passing the sidecut stream into a stripping column; separating the sidecut stream within the stripping column into an overhead vapor stream comprising propylene and propane which is passed into the first fractionation column and a first net bottoms stream which is withdrawn from the process and is substantially free of propylene; withdrawing from the first fractionation column a second net bottoms stream which is substantially free of propylene and propane and which is rich in $C_6$-plus hydrocarbons; and, forming a net overhead liquid stream which comprises propane and propylene from an overhead vapor stream removed from the first fractionation column, and passing the net overhead liquid stream into the catalytic condensation reaction zone as the previously referred to net fractionation column overhead stream.

I claim as my invention:

1. A hydrocarbon conversion process which comprises the steps of:

(a) passing a feed stream comprising propylene and propane, a hereinafter characterized recycle stream which also comprises propane and propylene and a hereinafter characterized first net fractionation column overhead stream into a catalytic condensation reaction zone wherein the entering hydrocarbons are contacted with a catalyst at conditions effective to produce a reaction zone effluent stream which comprises propane, propylene and $C_6$-plus hydrocarbons;

(b) separating the reaction zone effluent stream into a vapor-phase stream, which is returned to the catalytic condensation reaction zone as said recycle stream, and a liquid-phase stream comprising propane, propylene and $C_6$-plus hydrocarbons;

(c) passing the liquid-phase stream into a first fractionation column;

(d) passing a sidecut stream comprising propane and propylene and which is withdrawn above the feed point of the first fractionation column into a stripping column wherein the sidecut stream is separated into a second net overhead stream which is passed into the first fractionation column and a first net bottoms stream which is substantially free of propylene, and withdrawing the first net bottoms stream from the process;

(e) withdrawing from the first fractionation column a second net bottoms stream which is substantially free of propane and which comprises $C_6$-plus hydrocarbons; and, (f) forming a net overhead liquid stream which comprises propane and propylene from an overhead vapor stream removed from the first fractionation column, and passing the net overhead liquid stream into the catalytic condensation reaction zone as the previously referred to first net fractionation column overhead stream.

2. The process of claim 1 further characterized in that the feed stream is substantially free of ethane.

3. The process of claim 1 further characterized in that the feed stream comprises propylene and butylene.

4. The process of claim 1 further characterized in that an SPA-type catalyst is employed in the reaction zone.

5. The process of claim 3 further characterized in that the vapor-phase stream derived from the reaction zone effluent stream is condensed and the resultant condensate is returned to the catalytic condensation reaction zone as the previously referred to recycle stream.

6. A hydrocarbon conversion process which comprises the steps of:

(a) passing a feed stream comprising propylene and propane, a hereinafter characterized recycle stream, and a hereinafter characterized net fractionation column overhead stream into a catalytic condensation reaction zone wherein propylene is contacted with a catalyst at conditions effective to produce a reaction zone effluent stream comprising propylene, propane and $C_6$-plus hydrocarbons;

(b) cooling and then flashing the reaction zone effluent stream to a pressure below the pressure maintained in the reaction zone;

(c) separating the reaction zone effluent stream in a vapor-liquid separation zone into a vapor-phase stream comprising propylene and propane and a liquid-phase stream comprising $C_6$-plus hydrocarbons, propane and propylene;

(d) passing the contents of the vapor-phase stream into the catalytic reaction condensation zone as the previously referred to recycle stream;

(e) passing the liquid-phase stream into a first intermediate point of a first fractionation column;

(f) withdrawing a sidecut stream comprising propane and propylene from the first fractionation column at a higher second intermediate point and passing the sidecut stream into a stripping column;

(g) separating the sidecut stream within the stripping column into an overhead vapor stream comprising propylene which is passed into the first fractionation column and a first net bottoms stream which is withdrawn from the process and is substantially free of propylene;

(h) withdrawing from the first fractionation column a second net bottoms stream which is substantially free of propylene and propane and which is rich in $C_6$-plus hydrocarbons; and, (i) forming a net overhead liquid stream which comprises propane and propylene from an overhead vapor stream removed from the first fractionation column, and passing the net overhead liquid stream into the catalytic condensation zone as the previously referred to net fractionation column overhead stream.

7. The process of claim 6 further characterized in that the second net bottoms stream comprises butane derived from the feed stream and is passed into a second fractionation column.

8. The process of claim 6 further characterized in that the vapor stream removed from the vapor-liquid separation zone is condensed, admixed into a mixture of the feed stream and the net fractionation column overhead stream, and then the resultant admixture is heat exchanged against the reaction zone effluent stream prior to the flashing of the reaction zone effluent stream.

9. The process of claim 6 further characterized in that the feed stream comprises a mixture of propylene and butylene.

10. The process of claim 6 further characterized in that an SPA-type catalyst is present within the catalytic condensation zone.

* * * * *